United States Patent [19]

Schram

[11] Patent Number: 4,879,011

[45] Date of Patent: Nov. 7, 1989

[54] PROCESS FOR CONTROLLING A REACTION BY ULTRASONIC STANDING WAVE

[75] Inventor: Cornelius J. Schram, Pavenham, England

[73] Assignee: National Research Development Corporation, London, England

[21] Appl. No.: 229,495

[22] Filed: Aug. 8, 1988

[30] Foreign Application Priority Data

Aug. 7, 1987 [GB] United Kingdom ............ 8718756

[51] Int. Cl.[4] ........................................ B01J 19/08
[52] U.S. Cl. .................... 204/157.42; 204/157.62; 204/193
[58] Field of Search ............... 204/157.92, 157.62, 204/157.15, 193

[56] References Cited

U.S. PATENT DOCUMENTS 4,688,199 8/1987 Lock ............................ 367/137
4,743,361 5/1988 Schram ............................ 209/1

Primary Examiner—John F. Niebling
Assistant Examiner—Ben C. Hsing
Attorney, Agent, or Firm—Cushman, Darby & Cushman

[57] ABSTRACT

Particulate material is supported in a fluid medium by means of an ultrasonic standing wave while a reaction is effected or controlled involving the material so supported, for example with the fluid medium or other material contained in the medium. In a preferred arrangement, the standing wave is established by opposed ultrasonic transducers producing convergent beams that compensate for attenuation of the ultrasonic energy in the fluid medium, and operating in the near field. The support provided by the standing wave is able to avoid settling of the particulate material in the medium and also agitates the material; both effects enhance the rate of chemical reaction and help to ensure that the particulate material is more uniformly exposed. The process has particular applications to biological reactions, such as fermentation, and to chromatography, as examples.

19 Claims, 1 Drawing Sheet

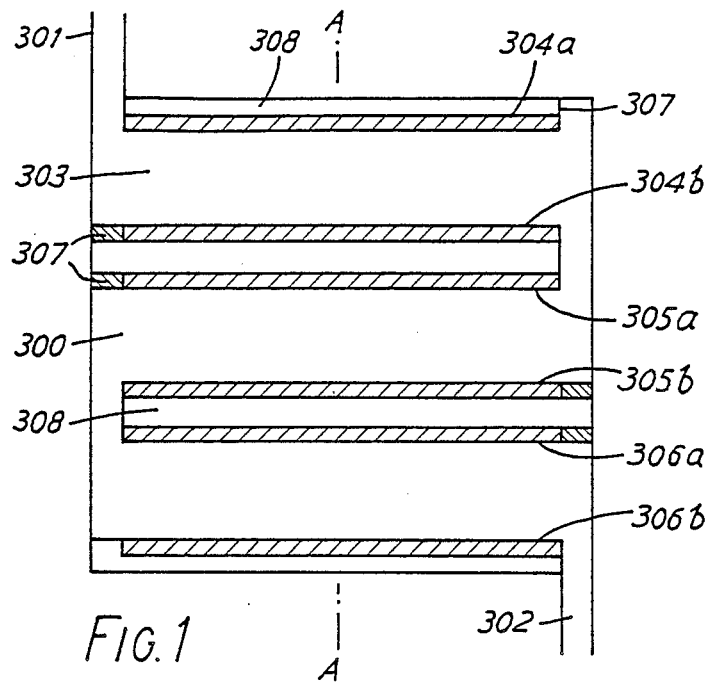
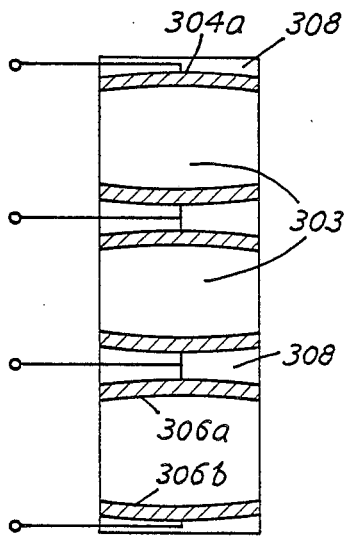
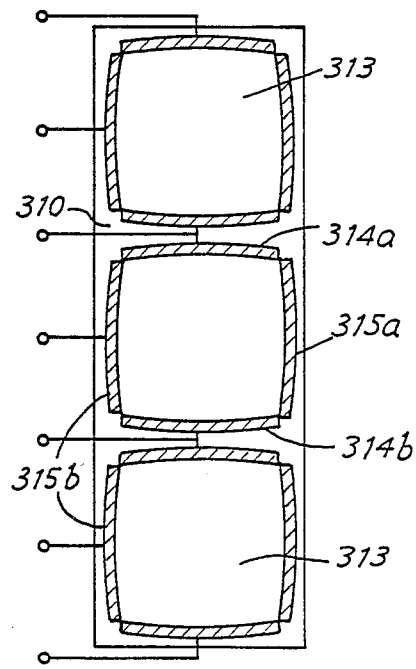
FIG.1
FIG.2
FIG.3

PROCESS FOR CONTROLLING A REACTION BY ULTRASONIC STANDING WAVE

BACKGROUND OF THE INVENTION

The present invention relates to a method of and means for enabling or controlling a reaction between particulate material and a reactant in a fluid medium in which said material is immersed. The reactions with which the invention may be concerned include chemical and biological processes and more generally may be any kind of process which relies on intimate mixing of two or more agents, one or both of which may be in particulate form, to effect some action between the agents.

When a material in particulate form is put in contact with another substance to undergo a chemical reaction, the efficiency of the reaction may be limited by the difficulty of ensuring that the particles are fully exposed to the reactant. Particularly if the product of the reaction is itself a solid, without special measures to prevent it acting as a barrier it may be possible to expose and react only a small proportion of the particulate material.

Mechanical stirring and agitating procedures are used to promote mixing, of course, and in recent years fluidised beds have been used to generate more intense reaction processes, but these known methods have a number of disadvantages and limitations. For example, although an object may be to obtain relative displacement between the particulate material and the fluid, if agitation of the particles is applied through the fluid the efficiency of mixing is limited, especially with mechanical mixing methods. To the extent that gravitational forces play any part, these are relatively weak and cannot be controlled; indeed their effects are dependent on the densities of the materials being processed. In the case of fluidised beds, moreover a minimum bed thickness is needed which can lead to clumping of the particulate matter even though a better mixing can be obtained than by mechanical methods.

SUMMARY OF THE INVENTION

According to the present invention, there is provided a process for controlling a reaction involving particulate material immersed in a fluid medium, characterised in that an ultrasonic standing wave is established within the medium to retain said particulate material suspended in the medium and there is relative displacement between said material and the fluid medium, whereby to effect or control the reaction.

The invention can be applied to achieving many different types of reaction. Thus, reactions may be performed that rely on the presence of an external energy field with the fluid medium, which may itself act simply as an inert carrier; one example of this is the polymerisation of monomer droplets held stationary by the standing wave in a moving fluid stream to be exposed to ultra-violet light, the characteristics of the standing wave being so chosen that its influence on the larger polymerised molecules is weakened, allowing them to be swept away with the moving fluid for collection.

A particularly important group of processes with which the present invention is concerned involves reactions between the particulate material and the fluid medium itself or other material contained in the medium. By retaining the particulate matter at the nodes of a standing wave established within a zone in the reaction vessel, motion of the fluid past the particulate material can considerably facilitate chemical reactions associated with the contact therebetween. The fluid motion may involve recirculation or replenishment. A continuous supply of "fresh" or unreacted material can be presented to the particulate material and reaction products can be flushed away from the concentration of particulate material with the movement of the fluid.

In the following discussion of the action of a standing wave upon suspended particles, those stations along the axis of propagation of the acoustic energy which the adjacent net acoustic forces act towards are termed nodes and those which said acoustic forces act away from are termed antinodes, and it is indicated that the particles influenced by a standing wave will tend to accumulate at the nodes of the wave. It must be said, however, that the detailed theory underlying the observed phenomenon of standing waves and their effect of particles in fact is not fully understood, but any lack of theoretical understanding has no bearing on the practical application of the invention. In particular, unless stated otherwise, the term "nodes" as used herein may thus be considered to include both nodes and antinodes, because in practice it does not appear to matter to the results that can be achieved.

The acoustic forces acting on a particle that is small compared to the wavelength of a standing wave tend to urge the particle to the nearest node. If there is an axial opposing force less than the maximum acoustic force, eg., from the movement of a liquid relative to the standing wave, the equilibrium position of the particle is displaced somewhat, although it still remains attached to the force field of the node. If the opposing force exceeds the maximum acoustic force, the particle is swept through the standing wave. Different particles may have different responses, both to the acoustic forces and the opposing forces, and so can be induced to move differentially in the standing wave. For the opposing force, any form of non-acoustic force can be used. For example, the effect of the standing wave can be opposed by gravity or an enhanced gravitational field, or other field forces such as electrostatic or electromagnetic forces may be appropriate. In the case of gravity, separation is not dependent on size but on other acoustic properties of the particles.

If a standing wave pattern is produced by overlapping progressive waves from two sources differing slightly in frequency, the standing wave will move towards the source emitting the lower frequency. Possibilities exist therefore both for holding particles fixed in space while they are suspended in a liquid, and also for moving them at a controlled rate, whether or not the liquid is itself moving. Reference may be made to U.S. Pat. No. 4,688,199 for an example of a means of achieving such controlled movement.

Using an axial opposing force such as the viscous drag of a liquid, it is possible to operate in a condition in which the position of the standing wave is fixed (ie., the array of nodes forming the standing wave is at least substantially motionless relative to the sources generating the standing wave) and the liquid flows axially to the standing wave. In this condition the nodes of the standing wave can be likened to a series of filters or grids holding the particulate material in a substantially constant position while the liquid passes this material with any other particles that are less strongly influenced by the acoustic forces. Alternatively, with the liquid stationary and the standing wave caused to move along its own axis, the nodes of the standing wave can be likened to a comb that is passed through the liquid carrying with it the particulate material. It will be understood that by combination of the movements of both the liquid and the standing wave, whether in the same sense or in countercurrent to each other, as well as by controlling the standing wave intensity and/or frequency, it is readily possible to achieve an extremely wide degree of control.

Although the particulate matter will be held in concentrations at the nodes of a standing wave, the nature of this restraint need not significantly impede axial flow of the fluid medium through this zone. Particles retained at the nodes are not held rigidly in a fixed position, but exhibit a rapid random motion of very small amplitude. This enables fluid media to flow through densely concentrated particulate matter in a manner which permits a more rapid diffusion, eg., of reagents or products, to and from that matter.

The present invention also comprises arrangements in which there is at least a component of fluid flow normal to the axis of the standing wave, in an extreme case the fluid flow being substantially at right-angles to the standing wave axis. The acoustic energy density in a nodal plane will generally not be uniform, and a particle influenced by the standing wave will move parallel to that plane in the direction of increasing energy density. The axial acoustic forces on particles in a standing wave which move them towards the nodes are normally very much greater than the acoustic forces parallel to the nodes of the standing wave, particularly at higher ultrasonic frequencies and particularly also when operating in the far field of the radiation. Particles can thus be displaced parallel to the nodal planes by a much smaller non-acoustic force than is needed to displace them axially of the standing wave. Processes according to the invention may accordingly rely on relative movement parallel to a standing wave axis or parallel to its nodal planes, or at angles oblique thereto.

BRIEF DESCRIPTION OF THE DRAWINGS

FIG. 1 is a longitudinal sectional view of one form of apparatus for performing the method according to the invention, FIG. 2 is a transverse sectional view on the plane A—A in FIG. 1, and FIG. 3 is a similar transverse sectional view illustrating a modification of the apparatus of FIGS. 1 and 2.

PREFERRED EMBODIMENTS OF THE INVENTION

A process in accordance with the invention may be applied to a very wide size range of particles, the upper size limit being determined primarily by the internodal distance in the standing wave because the acoustic forces on a particle will essentially cease to be effective when it is so large that it spans the distance between a node and the adjacent antinode. Among examples of suitable biological particles there can be considered animal cells, for instance mammalian cells, plant cells, micro-organisms and the spores of micro-organisms. Cell constituents such as nuclei, mitochondria and microsomes as well as plankton, yeasts, pollen, protozoa, richetsia and viruses, are further examples of biological particles applicable to the processes of the present invention. Outside the field of biological particles, the invention can be employed for the processing of many industrial particulates, including dispersions, suspensions and finely-divided precipitates, as well as dusts, and even liquid droplets. More generally, the invention may be applicable to a wide variety of chemical processes in which fluid media are in contact with particulate matter. For example, the particulate material retained in the standing wave can be a catalyst influencing a chemical reaction involving one or more other reactants. Such processes include enzymatic reactions in which the particulate material comprises one or more functional enzymes bound to particulate carrier material. Enzymes can also be located at the liquid/gas interface of bubbles.

In the performance of the invention, selection of the frequency and intensity of the standing wave will influence the character of particulate matter that is retained at the nodes and may be used to differentiate between particle types to segregate those types that are not required in the specific reaction. Such differentiation may be dependent on properties such as shape, density or size. For example, if the invention is used to retain propagating plant cells during the liquid suspension culture of such cells as part of a "cloning" process, as the plant cells cluster or exhibit cellular differentiation they can acquire substantially altered acoustic properties and can conveniently be swept away from the residual plant cells in the fermentation vessel for collection and further handling. Another example lies in chromatographic techniques involving the binding of material, dissolved or dispersed in the fluid medium, onto a particulate carrier held by the standing wave. When the carrier material has become loaded with bound material, its acoustic properties alter and the conditions of the standing wave may be set so that it is no longer held but can be swept away, eg., by the fluid flow, for collection and elution elsewhere to recover the bound material. If desired, a chromatographic technique of this type can be used in a "downstream" operation to recover dissolved/dispersed products of a process which involves particulate matter held at the nodes of a standing wave.

Another useful application of the invention is in essentially biological "fermentation" processes. In these processes particulate matter, eg., bacteria, yeasts, plant cells or animal cells, is cultivated in a fermentation vessel through which appropriate liquid media are circulated. Very favourable propagation conditions can be established if the cellular material is retained at the nodes of the standing wave within the fermentation vessel. Fresh reactant material can be presented readily to the cellular matter and spent material flushed away from the zone in which the cellular matter is retained. A uniform presentation of reactants can be made to the bulk of the cellular material, whereas in traditional fermentation vessels this may be more difficult. If the cellular matter is randomly distributed throughout the fermentation vessel and relies on stirring to effect an even distribution of fresh reactant to the cellular matter, such distribution is bound to be uneven in practice and undesirable local concentrations can occur. In a fermentation process in accordance with the present invention, fresh reactant can be presented to the cellular matter in an appropriate distribution leading to optimum propagation conditions.

The invention particularly facilitates the separation of desirable and/or undesirable products from the fermentation system. For example, soluble by-products of the fermentation reaction can be flushed away readily from the cellular matter. In a traditional fermentation process such by-products tend to accumulate in the vicinity of the cellular matter and often have an inhibiting effect on the continuance of the reaction. This is particularly disadvantageous where the by-product itself is a desired product of the process. By flushing such by-products away from the propagating cells, separation of the by-products from the fluid media can be conducted readily in a region remote from the propagating cells.

Another advantage of the invention when applied to fermentation reactions is that certain cell types, particularly mammalian cells, are induced to function more efficiently when in association with other similar cells. For example, it has already been established that hybridoma cells used in the manufacture of monoclonal antibodies, will only produce such antibodies efficiently in quantity when they can co-exist. Hybridoma cells in isolation do not function efficiently. The invention provides an efficient mechanism for concentrating hybridoma cells together in an environment in which relevant fluid agents can be passed through the concentration of the cells and optimum antibody production can be maintained. Experiments indicate that acoustic frequencies and energy densities can be employed which do not damage or interfere with the growth of such hybridoma cells.

In a further application of the invention the standing wave can be used as a means to remove reacted or spent particulate material from the reaction vessel, either occasionally during the course of the reaction, or at its termination. This can be achieved by giving the standing wave an axial movement to carry the particulate matter with it into a collection or exit zone from which the matter can be removed from the reaction vessel.

For the types of particles referred to above as examples, the optimum frequency needed to establish an appropriate standing wave in water will be in the range 100kHz to as high as 50MHz. In the upper end of this range it becomes increasingly important to consider the reduction of intensity of the ultrasonic radiation with distance from the source: because of this attenuation, the two progressive waves cannot be identical in amplitude except in a limited region. Away from that region there is a resultant radiation pressure which at any particular point will drive the fluid there away from the radiation source that happens to be dominant at that point, this movement being referred to herein as acoustic streaming.

Acoustic streaming can clearly have a disturbing effect on any attempt to control the movement of particles by means of the acoustic forces acting directly on them. It is inevitable when the standing wave is formed by interference between incident and reflected waves from a single source. When the standing wave is formed by interference between the outputs from two opposed sources, it is possible to balance out radiation pressure, at least in substance over a part of the distance between the sources, but that part of the distance becomes significantly smaller at higher ultrasonic frequency ranges such as are suitable for processing small particles.

Thus, for a standing wave in water at 20° C., Table 1 shows the total working distance available in mm within three different tolerance levels of imbalance for different frequencies, ignoring the effects of divergence:

TABLE 1

| Frequency MHz | Total working distance available (mm) Percent imbalance | | |
|---|---|---|---|
| | 5% | 2% | 1% |
| 0.3 | 11,400 | 4,400 | 2,200 |
| 1.0 | 1,000 | 400 | 200 |
| 3.0 | 114 | 44 | 22 |
| 10.0 | 10.3 | 4.0 | 2.0 |

Clearly, it would be desirable to avoid generating unbalanced radiation pressure within the liquid, or at least to keep such pressures so low to prevent any significant acoustic streaming, in order to maintain sufficiently uniform conditions in the maximum volume of the acoustic field.

According to a preferred feature of the present invention, the energy density of the acoustic field is rendered more uniform by forming a convergent beam from the or each ultrasonic source with an angle of convergence sufficiently great to at least substantially compensate for the attenuation of the acoustic energy in the fluid medium through which the beam is propagated. For more effective results, it will generally be desirable to apply a degree of convergence to the ultrasonic beam that is sufficient also to compensate for the normal divergence of the output from an ultrasonic source.

By these means it is thus possible to create a standing wave in an acoustic field in which there is no or only negligible acoustic streaming over a considerable axial distance, with the result that a much greater working volume can be made available for such operations as large quantities of particles in a reaction vessel through which a liquid is circulating.

The following example illustrates the use of the invention to mitigate the attenuation of a MHz ultrasound beam in water. In this medium at 20°, the attenuation A is given by the formula:

$$A = 25 \times 10^{-17} \times f^2 \qquad (1)$$

where f is the ultrasound frequency in MHz.

Thus, at 8 MHz, A=0.016.

If the energy densities at two points along the axis of propagation of the beam spaced d cms apart are $I_a$ and $I_b$, then the attenuation over that distance is given by the formula:

$$A = \frac{1}{2d} \log_e \left[ \frac{I_a}{I_b} \right]$$

Assume a working distance of 10 cm is required, then in order to balance the energy loss due to attenuation with the gain due to convergence (and ignoring any normal divergence of the beam):

$$\frac{I_a}{I_b} = 1.377$$

If a converging conical beam is established through which a cross-sectional normal to the axis of propagation at points 10 cm apart along that axis is in the ratio of 1.377:1, corresponding to a conical angle of convergence of approximately 2°, the resultant acoustic energy density will be substantially independent of position between the two points. It will be noted that the energy density falls logarithmically with distance and that the conical convergence of the ultrasonic beam therefore does not give an identical compensating gain. Over a finite working distance, however, it is possible to achieve a sufficiently close approximation. Similarly to the example above, it is possible to establish the corresponding angle for different frequencies in the same fluid medium, as follows:

TABLE 2

| MHz | in water at 20° C. |
|-----|--------------------|
| 5   | 0.37°              |
| 8   | 1.00               |
| 15  | 4.30               |
| 20  | 9.80               |
| 25  | 20.60              |
| 30  | 40.00              |

Although the usefulness of the procedure is more limited as frequency increases, because of the increasing angle of convergence, it can be seen that a valuable improvement in performance can be obtained at least up to the 25 MHz frequency.

By reducing or avoiding acoustic pressures over a longer axial distance, it is thus possible to establish very large arrays of nodal planes having constant energy density. For example, at 10 MHz in water at 20° C. there are 1350 nodes in 100 mm in the axial direction.

The means of producing convergent ultrasonic beams can be by employing shaped, ie., concave, transducer emitting surfaces, or by placing acoustic lenses in the path of transmission from the energy source. In a preferred example of this latter alternative, planar transducers are employed, each bonded to one face of a block of metal, eg., aluminium alloy, the opposite face of which is contoured and in contact with the fluid medium so that the required convergence of the beam is established as the ultrasonic energy enters the fluid medium.

The effects of attenuation described above are of especial concern in the far field of a source. In the near field it may be less important to counter attenuation and there are other factors in favour of operation in the near field for the purposes of the present invention.

As is known at a point in space close to a radiating surface, the emissions from that surface will have significant phase differences due to the Fresnel diffraction pattern. This creates in the near field a complex pattern of domains of high and low acoustic energy density. With increase of distance from the radiation source, that no longer happens and in the far field, in which a Fraunhofer diffraction pattern is established, the acoustic field is uniform, decreasing slowly in dependence on beam spread and attenuation. The near field is thus characterised by relatively large and non-uniform energy gradients.

By matching adequately the energy distribution from one transducer in the near, Fresnel field by that from a second transducer placed closed to and in face to face relation with the first transducer, a standing wave is produced, but one having a varying acoustic density pattern. That is to say, normal to the standing wave axis intense energy density gradients will be formed which will increase the tendency of particles to be held in the standing wave but will at the same time encourage the mobility of those particles within the standing wave.

It is to be understood that although the standing wave does not have the Fraunhofer diffraction pattern, the particles influenced by the energy density gradients are grouped in planar regions that can be identified as the nodal planes of the field, albeit that there are wider variations of energy density in these planes by virtue of the Fresnel diffraction fields that prevail.

The generation of a standing wave has been described in terms of interacting the outputs of two opposed sources. It is to be understood that other methods are possible and, as is known per se, a standing wave can be formed by interaction of incident and reflected beams from a single source. In the context of the present invention, it may be particularly appropriate to form a standing wave by reflection if operating in the near field or if measures are taken to limit streaming.

By way of further example, reference will now be made to the accompanying schematic drawings.

Referring to FIGS. 1 and 2, a reaction vessel 300 has a liquid inlet 301 and outlet 302. The interior of the vessel is divided into a series of parallel spaces 303 by opposed pairs of ultrasonic transducers 304a, 304b, 305a, 305b, 306a, 306b. Each pair of transducers is driven to establish an ultrasonic standing wave in the respective space 303.

The transducers, which are conveniently of a lead zirconate titanate ceramic, have slightly convex emitting surfaces, as can be seen in FIG. 2, to propagate a slightly convergent ultrasonic beam into the space 303. They may be constructed in manner already described, by abutting the ceramic emitter against a metallic coupling block, the emitting surface of which is given the curvature that produces the convergent beam. The degree of convergence is such that the energy density of the wave is constant with increasing distance from its transducer across the space 303. Consequently, the interference of the two beams from each opposed pair of transducers produces a standing wave free of any significant degree of acoustic streaming over the greater part of the distance between the opposed transducers. A nodal array is thus established in each space 303 in which particulate matter can be retained for reaction with the fluid in the chamber, or other matter contained therein.

By the use of baffles 307 the spaces 303 are connected in series to form a serpentine path through the vessel between inlet and outlet 301,302, the spaces 308 behind the transducers being sealed from the fluid flow, and possibly being air-filled. It will be obvious that with rearrangement of the baffles, the spaces 303 between the transducers of each pair can be connected in parallel if required.

Taking as an example the use of the apparatus in a bacterial fermentation process, the vessel 300 will be filled initially with a fluid culture medium incorporating a small population of the bacteria to be fermented. This composition is admitted to the vessel through inlet 301. (If desired, outlet 302 and inlet 301 can be linked through a recirculation system that is not shown). With the vessel filled with liquid the transducers 304–306 are activated and tuned to establish a stationary standing wave between the transducers of each pair having a frequency such that the bacteria are retained at the nodes of the standing waves. Regions of bacteria-rich medium are thus located in the vessel in the zones between the transducers of each pair. Nutrient medium is circulated through the bacteria-rich zones by means of the recirculation system and if necessary can periodically be replenished by admitting further nutrient medium and removing any excess medium.

In the steady state with, in effect, the whole population of bacteria as located firmly by means of the standing waves, nutrient medium can be drawn from the reaction vessel through the outlet 302 containing at most only a very low population of bacteria. By retaining the bacterial population at the nodes of the standing wave an efficient fermentation regime is established in which recirculation of the nutrient medium can readily distribute it uniformly to the bacteria. By-products can be removed from the fermentation system by flushing fresh nutrient medium into the reaction vessel without significant loss of bacteria through the outlet. On completion of the fermentation reaction, the bacterial population can be released by extinguishing the standing wave, and flushing the material from the reaction vessel through the outlet 302. Alternately, the contents of the reaction vessel containing the bacteria can simply be drained from the vessel.

FIG. 3 shows a modified arrangement in that each reaction space 313 in a chamber 310 is bounded by two pairs of opposed transducers 314a, 314b and 315a, 315b having shaped emitting surfaces and forming an essential rectangular cross-section fluid passage in which the two pairs of opposed transducers provide two standing wave patterns at right-angles to each other. Particles can thus be retained in relatively narrow regions at the intersection of the nodal planes of the two standing waves and the fluid directed through the passages flows parallel to these concentrations of particles. As in the preceding example, the curvature of the transducers is designed to give an essentially constant means acoustic energy density transversely of the passages and the passages can be connected together in series or in parallel.

It is a feature of the illustrated examples that the radiating surfaces of the transducers lie close to or bound the volume through which the standing wave extends. With this arrangement, the standing waves are established in the near fields of the transducers and relatively large acoustic pressure gradients occur within the standing wave. These gradients are non-uniform: they will exist in the flow direction of the passage as well as axially of the standing wave. Operating in near field conditions it may be possible to ignore the effects of streaming and employ planar transducers without any disadvantage. However, to the extent streaming in the axial direction of the standing wave may be unwanted, it can be supressed in substance as already described. Streaming in the flow direction of the liquid may even have beneficial results in encouraging agitation of the bacteria in the liquid medium.

It will be understood that it is possible to employ the process of the present invention with other modes of movement. In particular the matter retained at the nodes of a standing wave can be caused to progress at a controlled rate through a reaction chamber by producing a standing wave in which the nodes drift along the axis of propagation. In conjunction with this the fluid medium may have a flow velocity parallel and/or transverse to the axis of the standing wave. Some examples of chamber configurations that may be employed in a process according to the present invention can be seen in U.S. Pat. No. 4,743,361 and therefore do not need further illustration here.

The process of the present invention does not necessarily require active particulate material, such cells or insoluble enzyme complex particles, to be supported by the acoustic properties of these particles themselves. Instead, the standing wave can be utilised to support larger carrier particles to which cells, enzymes or other active elements can be attached by means known in the art. The standing wave system and the characteristics of the carrier particle may be chosen to match each other largely independently of the characteristics of the active particles, so as to generate a maximum response to the acoustic forces of the standing wave. As an example, cells such as hybridoma cells, which are obtained from the fusion of a mouse plasma cell and a mouse tumour cell and producing some specific immuno-reagent, can be attached to such carrier particles and thus be held substantially immobilised in a gentle current of liquid flowing parallel or transversely to the axis of the standing wave.

The carrier particles may be formed by any suitably inert material and may be given a variety of shapes. Fine fibrous elements having a large surface to volume ratio may be preferred for some purposes. There are also commercially available hollow glass microspheres ("Eccospheres"—Trade Mark) with a glass wall thickness of about 2 microns which, by virtue of their hollow construction, have a low specific gravity that may be a desirable quality for their manipulation in a carrier liquid. The glass walls of such particles are well suited to holding biologically active elements.

In the performance of the present invention it is also possible to provide for some degree of interaction between particles that are orientated and concentrated at the nodes of a standing wave. The interaction may be that of cell proliferation on closely positioned carrier particles at a node, possibly so that the growth forms bridges between neighbouring carrier particles. For example, if the beds of carrier particles are undisturbed for sufficient time in such conditions for the production of an immuno-reagent as referred to above, small mats of hybridoma cell tissue can be encouraged to form at the nodes, these mats resulting in much improved production of immunoglobulins, and yet by extinguishing the standing wave it is possible quickly and simply to replace or otherwise manipulate the whole culture.

I claim:

1. A process for controlling a reaction involving particulate material, in which said material is immersed in a fluid medium, an ultrasonic standing wave is established within said medium, said standing wave retaining said particulate material suspended in the medium, and a relative displacement is produced between said material and the fluid medium, whereby to effect or control the reaction.

2. A process according to claim 1 wherein a reaction is effected or controlled between the particulate material and a reactant fluid medium or other reactant material contained in the fluid medium while there is relative movement between said reactant and said particulate material.

3. A process according to claim 1 wherein the reaction occurs while the particulate material is retained in a substantially constant position at nodes of the standing wave and the fluid medium is caused to flow through a zone containing the retained particulate material.

4. A process according to claim 1 wherein the reaction occurs while the particulate material is held by nodes of a standing wave moving through a zone containing the fluid medium.

5. A process according to claim 1 wherein there is at least a component of fluid flow normal to the axis of the standing wave.

6. A process according to claim 1 wherein the ultrasonic frequency of the standing wave is in the range 100kHz50MHz.

7. A process according to claim 1 wherein the standing wave is generated by interference between two convergent beams, the angle of convergence of each being sufficiently great to at least substantially compensate for attenuation of the acoustic energy in the medium through which the beam is propagated.

8. A process according to claim 7 wherein an ultrasonic source produces at least one said beam and the convergence of the beam is increased to compensate also for the divergence energy output of the source.

9. A process according to claim 1 wherein said particulate material comprises a catalyst.

10. A process according to claim 1 wherein said particulate material comprises biological particles.

11. A process according to claim 10 wherein the biological particles are employed in a fermentation reaction.

12. A process according to claim 11 wherein said particles are held substantially fixed in the standing wave while by-products of the fermentation reaction are flushed away in a flow of the liquid medium through the standing wave.

13. A process according to claim 1 wherein the particulate material has its ultrasonic response modified by said reaction such as to change its mobility in the liquid medium.

14. A process according to claim 13 wherein said mobility change is employed to collect together the material so modified.

15. A process according to claim 13 wherein said mobility change is employed to provide a chromatographic response to bonding of the particulate material with a reagent.

16. A process according to claim 1 wherein the standing wave is employed to remove the particulate material after said reaction involving the material.

17. A process according to claim 1 wherein the particulate material comprises carrier particles to which is attached material for reaction with the fluid medium or other material carried therein.

18. A process according to claim 1 wherein cell proliferation or accumulation is carried out at nodes of the standing waves so as to form mat-like accretions of particulate material at the nodes.

19. A process according to claim 1 wherein standing waves on mutually transverse axes are established in a zone in which said reaction takes place, whereby to concentrate the particulate material in said zone towards the intersections of the nodes of the respective standing waves.

* * * * *